United States Patent
Kwon et al.

(10) Patent No.: US 11,134,878 B2
(45) Date of Patent: Oct. 5, 2021

(54) STRETCHABLE ELECTRODE SHEET AND STRETCHABLE WIRING SHEET, AND BIOLOGICAL INFORMATION MEASUREMENT INTERFACE

(71) Applicant: TOYOBO CO., LTD., Osaka (JP)

(72) Inventors: Euichul Kwon, Shiga (JP); Sonoko Ishimaru, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 1026 days.

(21) Appl. No.: 15/543,087

(22) PCT Filed: Jan. 13, 2016

(86) PCT No.: PCT/JP2016/050819
§ 371 (c)(1),
(2) Date: Jul. 12, 2017

(87) PCT Pub. No.: WO2016/114298
PCT Pub. Date: Jul. 21, 2016

(65) Prior Publication Data
US 2018/0020936 A1    Jan. 25, 2018

(30) Foreign Application Priority Data
Jan. 14, 2015  (JP) .............................. JP2015-004913

(51) Int. Cl.
*A61B 5/25* (2021.01)
*H01B 5/14* (2006.01)
(Continued)

(52) U.S. Cl.
CPC ............... *A61B 5/25* (2021.01); *A61B 5/291* (2021.01); *A61B 5/6804* (2013.01); *H01B 1/02* (2013.01);
(Continued)

(58) Field of Classification Search
CPC ... A61B 2562/164; A61B 5/04; A61B 5/0408; A61B 5/0478; A61B 5/68; A61B 5/6802;
(Continued)

(56) References Cited

U.S. PATENT DOCUMENTS 6,309,563 B1   10/2001   Lino et al.
10,119,045 B2  11/2018   Kondo et al.
(Continued)

FOREIGN PATENT DOCUMENTS

CN    201524078    7/2010
CN    102483972    5/2012
(Continued)

OTHER PUBLICATIONS

English (Machine) Translation of JP5448736, Mar. 19, 2014, 12 pages (translation retrieved from Google Patents) (Year: 2014).*
Office Action dated Jul. 17, 2019 in related U.S. Appl. No. 15/543,295.
Notification of Reasons for Refusal dated Nov. 26, 2019 in corresponding Japanese Application No. 2018-039114, with English translation.
(Continued)

*Primary Examiner* — Ronald Hupczey, Jr.
*Assistant Examiner* — Bradford C. Blaise
(74) *Attorney, Agent, or Firm* — Weneroth, Lind & Ponack, L.L.P.

(57) ABSTRACT

A stretchable conductive sheet comprising a first insulating layer and a stretchable conductor layer provided on the first insulating layer, wherein the stretchable conductor layer has an electric resistance of 300 Ω/cm or less, and a load at stretching of a stretching rate of 10% of the conductive sheet is 100 N or less.

13 Claims, 1 Drawing Sheet

(51) Int. Cl.
  *H01B 1/22* (2006.01)
  *A61B 5/291* (2021.01)
  *A61B 5/00* (2006.01)
  *H01B 1/02* (2006.01)

(52) U.S. Cl.
  CPC ............... *H01B 1/22* (2013.01); *H01B 5/14* (2013.01); *A61B 5/68* (2013.01); *A61B 5/6802* (2013.01); *A61B 2562/164* (2013.01)

(58) Field of Classification Search
  CPC ... A61B 5/6804; A61B 5/6805; A61B 5/6806; A61B 5/6807; H01B 5/14
  See application file for complete search history.

(56) References Cited

U.S. PATENT DOCUMENTS

| | | | |
|---|---|---|---|
| 2003/0054165 | A1 | 3/2003 | Yamanaka et al. |
| 2005/0095406 | A1 | 5/2005 | Gunzel et al. |
| 2005/0277826 | A1 | 12/2005 | Dunseath, Jr. |
| 2007/0078324 | A1* | 4/2007 | Wijisiriwardana ............ A41D 13/1281 600/386 |
| 2007/0119539 | A1 | 5/2007 | Gunzel et al. |
| 2008/0312523 | A1 | 12/2008 | Dunseath |
| 2009/0054758 | A1 | 2/2009 | Dunseath |
| 2009/0117362 | A1 | 5/2009 | Schosseler et al. |
| 2010/0234715 | A1 | 9/2010 | Shin et al. |
| 2010/0255742 | A1 | 10/2010 | Yuri et al. |
| 2012/0119626 | A1 | 5/2012 | Takahashi et al. |
| 2012/0152599 | A1 | 6/2012 | Kitagawa et al. |
| 2013/0019383 | A1 | 1/2013 | Korkala et al. |
| 2013/0056249 | A1 | 3/2013 | Taguchi et al. |
| 2013/0123601 | A1 | 5/2013 | Lindberg et al. |
| 2013/0225966 | A1 | 8/2013 | Maciá Barber et al. |
| 2013/0338472 | A1 | 12/2013 | Maciá Barber et al. |
| 2014/0124257 | A1 | 5/2014 | Yoshihara et al. |
| 2014/0202744 | A1 | 7/2014 | Kobayashi et al. |
| 2014/0291589 | A1 | 10/2014 | Hata et al. |
| 2014/0318699 | A1 | 10/2014 | Longinotti-Buitoni |
| 2015/0204697 | A1 | 7/2015 | Taguchi et al. |
| 2016/0130471 | A1 | 5/2016 | Burrows et al. |
| 2017/0002181 | A1 | 1/2017 | Lehmann et al. |
| 2017/0188949 | A1 | 7/2017 | Macia Barber et al. |
| 2017/0224244 | A1 | 8/2017 | Kuwabara et al. |
| 2017/0296123 | A1 | 10/2017 | Macia Barber et al. |
| 2018/0020936 | A1 | 1/2018 | Kwon et al. |
| 2019/0077930 | A1 | 3/2019 | Irie et al. |

FOREIGN PATENT DOCUMENTS

| | | |
|---|---|---|
| EP | 0 892 027 | 1/1999 |
| JP | 6-263899 | 9/1994 |
| JP | H10-95962 | 4/1998 |
| JP | 2000-133055 | 5/2000 |
| JP | 2001-126541 | 5/2001 |
| JP | 2004-288956 | 10/2004 |
| JP | 2004-288957 | 10/2004 |
| JP | 2007-509779 | 4/2007 |
| JP | 2007-173226 | 7/2007 |
| JP | 2007-263833 | 10/2007 |
| JP | 2008-501453 | 1/2008 |
| JP | 2008-198425 | 8/2008 |
| JP | 2010-189795 | 9/2010 |
| JP | 2011-15817 | 1/2011 |
| JP | 2012-33674 | 2/2012 |
| JP | 2012-54192 | 3/2012 |
| JP | 2012-138260 | 7/2012 |
| JP | 2012-181084 | 9/2012 |
| JP | 2012-183302 | 9/2012 |
| JP | 3178230 | 9/2012 |
| JP | 2012-231018 | 11/2012 |
| JP | 2012-248399 | 12/2012 |
| JP | 2013-135358 | 7/2013 |
| JP | 2013-184024 | 9/2013 |
| JP | 5448736 | 3/2014 |
| JP | 2014-510596 | 5/2014 |
| JP | 2014-137860 | 7/2014 |
| JP | 2014-151018 | 8/2014 |
| JP | 2014-200559 | 10/2014 |
| JP | 2014-228507 | 12/2014 |
| WO | 2011/145411 | 11/2011 |
| WO | 2012/108502 | 8/2012 |
| WO | 2013/031958 | 3/2013 |
| WO | 2013/146254 | 10/2013 |
| WO | 2014/153896 | 10/2014 |
| WO | 2014/178207 | 11/2014 |
| WO | 2016/114298 | 7/2016 |

OTHER PUBLICATIONS

Notification of Reasons for Refusal dated Nov. 26, 2019 in corresponding Japanese Application No. 2018-166995, with English translation.
Extended European Search Report dated Nov. 21, 2019 in corresponding European Application No. 17738393.2.
Notice of Reasons for Refusal dated Dec. 3, 2019 in corresponding Japanese Application No. 2018-039116, with English translation.
Notice of Reasons for Refusal dated Dec. 3, 2019 in corresponding Japanese Application No. 2018-039119, with English translation.
Submission of Information by Third Parties dispatched on Sep. 12, 2017 in Japanese Application No. 2016-569476, with English translation.
Submission of Information by Third Parties dispatched on Sep. 12, 2017 in Japanese Application No. 2016-569498, with English translation.
Office Action dated May 28, 2019 in corresponding Japanese Patent Application No. 2018-166995, with English Translation.
Office Action dated Jun. 4, 2019 in corresponding Japanese Patent Application No. 2018-011962, with English Translation.
Notification of Reasons for Refusal dated Feb. 18, 2020 in corresponding Japanese Patent Application No. 2019-034519, with English translation.
Office Action dated Feb. 26, 2019 in corresponding Japanese patent application No. 2018-039114, with English Translation.
European Office Action dated Apr. 18, 2019 in corresponding European patent application No. 16737369.5.
Office Action dated Nov. 4, 2019 in corresponding Chinese Parent Application No, 201680005764.7 with English translation.
Communication pursuant to Article 94(3) dated Nov. 5, 2019 in corresponding European Patent Application No. 16737369.5.
Office Action dated Mar. 5, 2019 in Japanese Patent Application No. 2018-039116, with English translation.
Office Action dated Mar. 5, 2019 in Japanese Patent Application No. 2018-039119, with English translation.
Office Action dated Mar. 12, 2019 in Japanese Patent Application No. 2018-039117, with English translation.
Decision of Refusal dated Jul. 28, 2020, in corresponding Japanese Patent Application No. 2018-166995, with English translation.
Paul et al., "An investigation into the durability of screen-printed conductive tracks on textiles", Measurement Science and Technology, 25:1-11 (2014).
Third Party Observation submitted Feb. 2, 2017 in corresponding International (PCT) Application No. PCT/JP2016/050819, with English Translation.
International Search Report dated Mar. 29, 2016 in International (PCT) Application No. PCT/JP2016/050936.
Third Party Observation dated Feb. 14, 2017 in International (PCT) Application No. PCT/JP2016/050936, with English Translation.
Inoue et al., "Application of Printing Process to Fabrication of E-textiles", Journal of the Surface Finishing Society of Japan, 64(11):577-581 (2013), with Partial English Translation.
International Search Report dated Apr. 19, 2016 in corresponding International (PCT) Application No. PCT/JP2016/050819.
Office Action dated May 29, 2018 in Japanese Application No. 2016-569498, with English translation.

(56) References Cited

OTHER PUBLICATIONS

Office Action dated Nov. 27, 2018 in corresponding Japanese patent application No. 2018-011962, with English translation.
Decision of Rejection dated Dec. 4, 2018 in corresponding Japanese patent application No. 2016-569476, with English translation.
Tada Yasunori, "A Characteristic Evaluation of an Undershirt for Measurement of Bioelectricity Using Conductive Ink Wires", Journal of textile Engineering, Jul. 2013, vol. 59, No. 6, p. 141-148.
International Search Report dated Apr. 18, 2017 in International (PCT) Application No. PCT/JP2017/000499.
Ahn et al., "Stretchable electronics: materials, architectures and integrations", Journal of Physics D: Applied Physics, vol. 45, 2012, 103001, pp. 1-14.
Chun et al., "Highly conductive, printable and stretchable composite films of carbon nanotubes and silver", Nature Nanotechnology, vol. 5, Dec. 2010, pp. 853-857.
Japanese Office Action dated Feb. 12, 2019 in corresponding Japanese patent application No. 2018-039115, with English translation.
Extended European Search Report dated Jul. 19, 2018 in corresponding European Application No. 16737369.5.
Office Action dated Aug. 7, 2018 in corresponding Japanese Application No. 2016-569476, with English translation.
Office Action dated Aug. 27, 2019 in Japanese Patent Application No. 2018-166996 with English translation.
Notice of Reasons for Refusal dated Mar. 2, 2021, in corresponding Japanese Patent Application No. 2018-039116, with English Machine translation.

\* cited by examiner

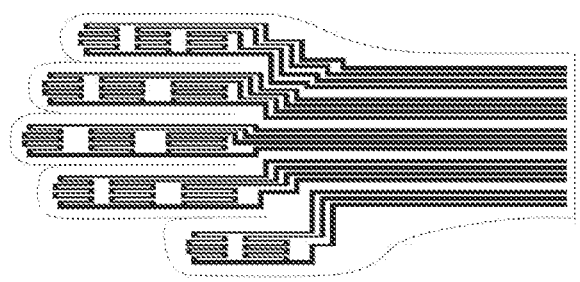

STRETCHABLE ELECTRODE SHEET AND STRETCHABLE WIRING SHEET, AND BIOLOGICAL INFORMATION MEASUREMENT INTERFACE

TECHNICAL FIELD

The present invention relates to a sheet-like stretchable electrode sheet and a stretchable wiring sheet, for wearable biological information measurement, that are capable of being laminated on a substrate, and a biological information measurement interface using the same.

BACKGROUND ART

Recently, wearable biological information measurement devices that may easily measure biological information such as electrocardiogram by being worn as a garment, belt, or strap have attracted attention in the medical field and the health monitoring field. For example, a user of a wearable measurement device for measuring electrocardiogram can easily understand the change of heart rate in a variety of situations in daily life by spending a day while wearing it as a garment.

Such a wearable biological information measurement device generally has electrodes, sensors corresponding to various measurements, and a wiring for transmitting those electrical signals to an arithmetic-processing unit or the like inside a garment made of a woven or knitted fabric.

As techniques for providing a wiring in the wearable biological information measuring device, a method including masking a region other than a region where the wiring is to be disposed on a fabric, and then applying a conductive polymer-containing paint to the fabric (Patent Document 1), and a method in which a silver paste layer sandwiched between urethane resin layers is formed on a fabric (Non-Patent Document 1) are proposed.

There are various known methods for incorporating an electrical wiring into a garment. Examples thereof include a method of forming a wiring on a fabric constituting a garment by printing using a conductive paste such as a silver paste, a method of weaving conductive fibers into a fabric, a method of embroidering a wiring with a conductive thread, a method of attaching or sewing a stretchable FPC (flexible printed circuit) processed in a separate step onto a garment, or the like.

RELATED ART DOCUMENTS

Patent Documents

Patent Document 1: JP-A-2014-151018

Non-Patent Documents

Non-Patent Document 1: Gordon Paul et al., Meas. Sci. Technol. 25 (2014)

DISCLOSURE OF THE INVENTION

Problems to be Solved by the Invention

However, the garment formed by the method described in Patent Document 1 may have a problem in that if the fabric is stretched when being actually worn, cracks are produced in a cured product of the conductive polymer forming a conductive layer, resulting in an interruption or block of electrical continuity. Furthermore, in the conductive fabric produced by the method described in Patent Document 1, since the conductive polymer-containing paint may permeate the inside of the fabric, it is hard to secure a satisfactory thickness of the conductive layer successively formed on the fabric, and although electrical conductivity to an extent required as an electrode can be achieved, it is difficult to achieve a high electrical conductivity required of a wiring.

Furthermore, the stretchability of the wiring described in Non-Patent Document 1 depends on the urethane resin layer, and the conductive layer has poor stretchability. A garment in which the wiring has been formed by the method described in Non-Patent Document 1 also has a problem in that if the fabric is stretched when being actually worn, the wiring cannot follow the elongation of the fabric, and cracks may be produced in the silver paste layer forming a conductive layer, resulting in an interruption or block of electrical continuity. When formed into an electrode, the surface of the electrode is not protected with the urethane resin layer, and therefore the generation of cracks due to the elongation of the garment is extensive as compared with the wiring.

The method of weaving conductive fibers into a fabric has low flexibility as to a shape of a wiring pattern, and is only used in a limited range of applications including the prevention of static charge, and hence it is insufficient as a wiring technique for widely incorporating electronic functions into clothes. In the method of embroidering a wiring with a conductive thread, although the wiring can be formed with high flexibility, this technique corresponds to a so called jungle wiring of the times when an electronic circuit was configured with a vacuum tube and has low productivity, and it is difficult to say that this technique can realize today's electronic functions. As a conductive fiber or conductive thread, one that has been plated with metal onto the surface of a fiber which is an insulating material, one in which a thin metal wire has been twisted into a thread, or one in which a conductive polymer is impregnated between fibers such as microfibers are known. Since these have generally insufficient conductivity and have circuit resistance in a distributed constant manner, the current capacity is small, resulting in the generation of delay and attenuation of signal transmission. Furthermore, according to the method of attaching or sewing a stretchable FPC (flexible printed circuit) processed in a separate step onto a garment, it is possible to incorporate a low-resistance wiring made of copper foil. Even if a stretchable material is used for a substrate portion of such a stretchable FPC, the wiring portion does not have intrinsic stretchability, and hence the stretchability is artificially realized by torsional deformation of the wire that is two-dimensionally distorted and arranged. For this reason, there is a problem with the durability of the copper foil, and in addition, clothes formed by this method produce strange feeling such as a coarse feel at the time of stretching and deformation and give a wearer a significantly uncomfortable feel.

The present invention has been made by focusing on the above situation, and an object of thereof is to provide a stretchable electrode and a stretchable wiring that are capable of maintaining high electrical conductivity even if being stretched, and biological information measurement interface in which the stretchable electrode and the stretchable wiring are laminated on a substrate such as a garment, belt, brassiere, or the like.

Means for Solving the Problems

The stretchable electrode and stretchable wiring of the present invention, which can accomplish the object described above, wherein the electrode and the wiring are sheet-like and that are capable of being laminated on a substrate comprising: wherein the electrode comprises a first insulating layer and a stretchable conductor layer provided on the first insulating layer, and the wiring has a three-layer structure comprising a first insulating layer, a stretchable conductor layer, and a second insulating layer, and wherein the stretchable conductor layer has an electric resistance of 300 Ω/cm or less, and a load at stretching of a stretching rate of 10% of the electrode and the wiring is 100 N or less.

Moreover, the stretchable electrode and the stretchable wiring of the present invention, which can accomplish the object described above, wherein the electrode and the wiring are sheet-like and that are capable of being laminated on a substrate comprising: wherein the electrode comprises a first insulating layer and a stretchable conductor layer provided on the first insulating layer, and the wiring has a three-layer structure comprising the first insulating layer, the stretchable conductor layer, and a second insulating layer, and wherein the stretchable conductor layer has an initial sheet resistance of 1Ω square or less and an initial electric resistance per wiring length of 300 Ω/cm or less, and a load at stretching of a stretching rate of 10% of the electrode and the wiring is 100 N or less. Here, Ω/cm means a resistance value per 1 cm of the wiring length. The initial sheet resistance of the stretchable conductor layer is preferably $1 \times 10^{-1}$ Ω square cm or less, more preferably $1 \times 10^{-2}$ Ω square cm or less, further preferably $1 \times 10^{-3}$ Ω square cm or less.

The stretchable electrode sheet and the stretchable wiring sheet of the present invention, wherein the electrode and the wiring preferably have a change in electric resistance at 20% stretching of less than 5-fold.

The stretchable conductor layer of the present invention preferably comprises a conductive filler and a resin.

The stretchable electrode sheet and the stretchable wiring sheet of the present invention preferably have a thickness of 200 μm or less.

The present invention further includes a biological information measurement interface comprising a substrate on which the stretchable electrode sheet and the stretchable wiring sheet of the present invention are laminated, wherein the substrate is a strip-shaped material such as a belt or a brassiere to be attached at least in a circumferential direction of a trunk of a human body, and/or a garment made of a woven or knitted fabric or a non-woven fabric.

Effects of the Invention

According to the stretchable electrode sheet and the stretchable wiring sheet of the present invention, the electric resistance of the stretchable conductor layer is 300 Ω/cm, a load at stretching of a stretching rate of 10% is 100 N or less, the change in electric resistance at 20% stretching is less than 5-fold, and high electrical conductivity can be held both at non-stretching and at stretching. Therefore, the biological information measurement interface produced using the stretchable electrode sheet and the stretchable wiring sheet makes it possible to be produced using a substrate having excellent stretchability, and since a load required for stretching is small, uncomfortable feeling that a movement of a wearer is excessively restrained by a garment when being worn is small, and it is possible to reduce an inhibition of wear comfort when being worn.

BRIEF DESCRIPTION OF THE DRAWINGS

The Drawing is a wiring pattern diagram printed on a glove exemplified in the present invention.

MODE FOR CARRYING OUT THE INVENTION

<Stretchable Electrode Sheet and Stretchable Wiring Sheet>

The stretchable electrode of the present invention is a sheet-like electrode including a first insulating layer and a stretchable conductor layer. The stretchable wiring sheet of the present invention is a sheet-like wiring including a first insulating layer, a stretchable conductor layer, and a second insulating layer.

<First Insulating Layer>

In the present invention, the first insulating layer acts as an adhesion surface when the stretchable electrode sheet and the stretchable wiring sheet are laminated on a substrate, and prevents moisture coming from the opposite side of the substrate on which the first insulating layer is laminated from reaching the stretchable conductor layer during wear. Although the stretchable conductor layer described later in the present invention has good stretchability, if the substrate is made of a material having excellent elongation property exceeding the stretchability of the stretchable conductor layer, it is thought that the stretchable conductor layer may be stretched following the elongation of the substrate, resulting in the production of cracks. The first insulating layer also serves as an elongation stopper to suppress the elongation of a fabric and prevent the stretchable conductor layer from being excessively elongated.

A resin forming the first insulating layer is not particularly limited as long as the resin has insulating property, and for example, polyurethane resin, silicone resin, vinyl chloride resin, epoxy resins or the like can be preferably used. Among these, polyurethane resin is more preferable in view of adhesive property with the stretchable conductor layer. Note that the resin forming the first insulating layer may be used singly, or in combination of two or more thereof.

Examples of the polyurethane resin include polyester resin, polyether resin, polycarbonate resin, and the like. Among these, polyester resin is preferable in view of stretchability of a coat.

As the resin forming the first insulating layer in the present invention, thermoplastic resins, thermosetting resins, rubbers, or the like having an elastic modulus of 1 to 1000 MPa can be used. In order to develop the film stretchability, rubbers are preferable. Examples of the rubbers include urethane rubber, acrylic rubber, silicone rubber, butadiene rubber, rubber containing a nitrile group such as nitrile rubber or hydrogenated nitrile rubber, isoprene rubber, vulcanized rubber, styrene-butadiene rubber, butyl rubber, chlorosulfonated polyethylene rubber, ethylene propylene rubber, vinylidene fluoride copolymer, and the like. Among these, rubber containing a nitrile group, chloroprene rubber, and chlorosulfonated polyethylene rubber are preferable, and rubber containing a nitrile group is particularly preferable. The elastic modulus in the present invention is preferably within a range of 3 to 600 MPa, more preferably 10 to 500 MPa, further preferably 30 to 300 MPa. It is preferred that the elastic modulus of the resin forming the first insulating layer be larger than the elastic modulus of the stretchable conductor layer in terms of the elongation stopping effect of stretchable conductor.

In the present invention, it is preferred that a load at stretching of a stretching rate of 10% of the first insulating layer be larger than a load at stretching of a stretching rate of 10% of the stretchable conductor layer.

The first insulating layer in the present invention can be formed by dissolving or dispersing the above-mentioned insulating resin in an appropriate solvent (preferably water) and applying or printing the resulting solution onto a release paper or release film to forma coat, followed by evaporating and drying the solvent contained in the coat. Alternatively, a commercially-available sheet or film having appropriate physical properties described later can be used.

The thickness of the first insulating layer is preferably 5 to 200 μm, more preferably 10 to 70 μm, further preferably 20 to 50 μm. If the first insulating layer is too thin, the insulation effect and the elongation stopping effect may become insufficient. On the other hand, if the first insulating layer is too thick, the stretchability of the fabric may be inhibited, and wear comfort may be inhibited since the thickness of the entire electrode and wiring increases.

<Stretchable Conductor Layer>

In the present invention, a stretchable conductor layer is formed on the first insulating layer. Electrical continuity is ensured by the stretchable conductor layer. The stretchable conductor layer preferably contains a conductive filler and a resin.

The conductive filler forming the stretchable conductor layer is preferably metal powder. If necessary, the conductive filler may include conductive materials or metal nanoparticles other than the metal powder.

Examples of the metal powder include noble metal powder such as silver powder, gold powder, platinum powder or palladium powder, and base metal powder such as copper powder, nickel powder, aluminum powder or brass powder, as well as plated powder wherein heterologous particles including base metal or inorganic substances such as silica are plated with noble metal such as silver, and base metal powder that is made into alloy using noble Metal such as silver. Among these, silver powder and copper powder are preferable from the viewpoint of easily developing high electrical conductivity and of the cost, and it is desired that silver powder and/or copper powder be contained as main ingredient(s) (50% by mass or more). Note that the conductive filler may be used singly, or in combination of two or more thereof.

Preferred shapes of the metal powder include known flakes (scales), spheres, dendrites, aggregates (a shape wherein spherical primary particles are aggregated into a three-dimensional shape), and the like. Among these, metal powder in flakes, spheres or aggregates is particularly preferred.

Particle diameter of the metal powder is preferably 0.5 to 10 μm in terms of an average particle diameter. When the average particle diameter is too large, it may become difficult to form a desired pattern shape when a wiring is formed in a fine pattern. On the other hand, when the average particle diameter is too small, it is not preferred that the metal powder be easily aggregated in the formation of the stretchable conductor layer, and the raw material cost increase with decreasing the average particle diameter.

The amount ratio of the metal powder in the conductive filler is preferably 80% by volume or more, more preferably 85% by volume or more, and further preferably 90% by volume or more. If the amount ratio of the metal powder is too small, it may become difficult to develop sufficiently high electrical conductivity.

Note that when each ingredient is indicated in % by volume in the present invention, it can be obtained by measuring a mass of solid content of each ingredient contained in a paste and calculating a volume of solid content of each ingredient using the equation: (mass of each solid content÷specific gravity of each solid content).

Conductive particles (a) in the present invention are composed of a material having a specific resistance of $1\times10^{-1}$ Ωcm or less, and have a particle diameter of 100 μm or less. Examples of the material having a specific resistance of $1\times10^{-1}$ Ωcm or less include metal, alloy, carbon, doped semiconductor, conductive polymer, and the like. As the conductive particles preferably used in the present invention, metals such as silver, gold, platinum, palladium, copper, nickel, aluminum, zinc, lead, and tin, alloy particles such as brass, bronze, cupronickel, and solder, hybrid particles such as silver-coated copper, metal-plated polymer particles, metal-plated glass particles, metal-coated ceramic particles, and the like can be used.

In the present invention, it is preferred to mainly use flaky silver particles or an irregular-shaped aggregated silver powder. Here, the "mainly use" means that the amount of 90% by mass or more of the conductive particles is used. The irregular-shaped aggregated powder is made by three-dimensional aggregation of spherical or irregular-shaped primary particles. The irregular-shaped aggregated powder and the, flaky powder are preferable because they have a specific surface area larger than that of spherical powder or the like, and hence an electrical conductivity network can be formed even when the filling amount is small. The irregular-shaped aggregated powder, which is not in a monodisperse form, is further preferable because the particles physically contact with each other, and hence an electrical conductivity network can be easily formed.

Although there is no particular limitation for the particle diameter of the flaky powder, the average particle diameter (50% D) measured by a dynamic light scattering method is preferably 0.5 to 20 μm, and more preferably 3 to 12 μm. If the average particle diameter exceeds 15 μm, the formation of a fine wiring may become difficult, and clogging occurs in the case of screen printing or the like. If the average particle diameter is less than 0.5 μm, the particles cannot contact with each other when the filling amount is small, and as a result, the electrical conductivity may deteriorate.

Although there is no particular limitation for the particle diameter of the irregular-shaped aggregated powder, the average particle diameter (50% D) measured by a light scattering method is preferably 1 to 20 μm, and more preferably 3 to 12 μm. If the average particle diameter exceeds 20 μm, the dispersibility decrease, and as a result, paste formation may become difficult. If the average particle diameter is less than 1 μm, the effects as the aggregated powder is lost, and as a result, high electrical conductivity may not be maintained when the filling amount is small.

As to the conductive material, for example, a carbon nanotube is preferred, and a carbon nanotube having a mercapto group, amino group, or nitrile group on its surface, or a carbon nanotube that is surface-treated with a rubber having a sulfide bond and/or nitrile group is particularly preferred. Generally, a conductive material itself has strong cohesive force, and in particular, a conductive material having a high aspect ratio as described later has a low dispersibility in the resin. However, when the conductive material has a mercapto group, amino group or nitrile group on its surface or is surface-treated with a rubber having a sulfide bond and/or nitrile group, affinity to the metal powder increases, and an effective electrically conductive network can be formed together with the metal powder, whereby high electrical conductivity can be realized.

A carbon nanotube has a structure wherein a two-dimensional graphene sheet is rolled in a tubular shape. Depending on the layer numbers and the front end shape, it is divided into multi-wall type, single-wall type and horn type. Moreover, depending on the rolling method of the graphene sheet, it is divided into three types which are armchair type structure, zigzag type structure and chiral type structure. In the present invention, any types of carbon nanotubes may be used. The diameter of the carbon nanotube is not particularly restricted, and is preferred to be 0.5 to 200 nm.

A method for introducing a functional group (mercapto group, amino group, or nitrile group) onto the surface of a carbon nanotube is not particularly limited, and known methods such as a method wherein reaction is carried out and introduction is done by means of covalent bond, a method wherein hydrophobic interaction and/or hydrogen bond are/is utilized, a method wherein π-stacking is utilized, and a method wherein electrostatic interaction is utilized may be used.

As to a method for surface-treating a carbon nanotube with a rubber containing a sulfide bond and/or nitrile group, the functional group introduced onto the surface of a carbon nanotube by any of the above-mentioned methods has only to allow to react with a predetermined rubber having a reactive group, so that the predetermined rubber can be attached to the surface of the carbon nanotube.

It is preferred that the conductive material have an aspect; ratio of 10 to 10,000. In particular, when the conductive material is a carbon nanotube, the aspect ratio is preferably 20 to 10,000, and more preferably 50 to 1,000. The conductive materials having such aspect ratios can develop higher electrical conductivity.

The amount ratio of the conductive material in the conductive filler is preferably 20% by volume or less, more preferably 15% by volume or less, and further preferably 10% by volume or less. If the amount ratio of the conductive material is too large, it may become difficult to uniformly disperse it in the resin. Moreover, the above-mentioned conductive materials are usually expensive. For these reasons, it is desired to reduce the use amount of the conductive material to the above-mentioned range.

As to the metal nanoparticles, there are exemplified silver, bismuth, platinum, gold, nickel, tin, copper and zinc. The average particle diameter of the metal nanoparticles is preferably 2 to 100 nm. In particular, in view of the electrical conductivity, copper, silver, platinum and gold are preferable, and the metal nanoparticles that contain silver and/or copper as main ingredient(s) (50% by mass or more) are more preferable. The inclusion of the metal nanoparticles is expected to enhance the electrical conductivity, and in addition, contributes to rheology adjustment of a conductive paste used for forming a stretchable conductor layer, whereby the printing property can be improved.

The amount ratio of the metal nanoparticles in the conductive filler is preferably 20% by volume or less, more preferably 15% by volume or less, and further preferably 10% by volume or less. If the amount ratio of the conductive materials is too large, the metal nanoparticles tend to easily aggregate in the resin. Moreover, the metal nanoparticles having a small particle diameter as described above are usually expensive. For these reasons, it is desired to reduce the use amount of the metal nanoparticles to the above-mentioned range.

The content of the above-mentioned conductive filler in the stretchable conductor layer (that is, the content of the conductive filler in total solid matters in a conductive paste for forming the stretchable conductor layer) is preferably 15 to 45% by volume, and more preferably 20 to 40% by volume. If the content of the conductive filler is too small, the electrical conductivity may be insufficient. On the other hand, if the content of the conductive filler is too large, the stretchability of the stretchable conductor layer tends to decrease, and cracks are generated upon stretching the resulting the stretchable electrode sheet and the stretchable wiring sheet. As a result, good electrical conductivity may not be maintained.

The resin forming the stretchable conductor layer preferably contains at least a rubber containing a sulfur atom and/or a rubber containing a nitrile group. The sulfur atom and the nitrile group have high affinity to metal, and the rubber has high stretchability whereby the generation of cracks and the like can be avoided even upon being stretched. Therefore, even if the electrode sheet and the wiring sheet are stretched, the conductive filler can be held in a uniformly dispersed state, and excellent electrical conductivity can be developed. From the viewpoint of a change in electric resistance at stretching, the rubber containing a nitrile group is more preferable. Note that the resin forming the stretchable conductor layer may be used singly, or in combination of two or more thereof.

There is no particular limitation for the rubber containing a sulfur atom as far as it is a rubber or elastomer containing sulfur. The sulfur atom can be contained in a form such as a sulfide bond or disulfide bond in a main chain of a polymer or as a mercapto group in a side chain or terminal of a polymer. Specific examples of the rubber containing a sulfur atom include polysulfide rubber, polyether rubber, polyacrylate rubber, and silicone rubber that contain a mercapto group, sulfide bond or disulfide bond. In particular, polysulfide rubber, polyether rubber, polyacrylate rubber and silicone rubber that contain a mercapto group are preferred. It is also possible to use a resin in which a sulfur-containing compound such as pentaerythritol tetrakis(S-mercaptobutyrate), trimethylolpropane tris(S-mercaptobutyrate), mercapto group-containing silicone oil, etc. is compounded into a rubber having no sulfur atom. As commercial products that may be used as the rubber containing a sulfur atom, "Thiokol (registered trademark) LP" manufactured by Toray Fine Chemical, which is a liquid polysulfide rubber, and the like are preferably given. The content of the sulfur atom in the rubber containing a sulfur atom is preferably 10 to 30% by mass.

It is preferred to use a flexible resin (c) as the resin in the present invention. As the flexible resin (c) in the present invention, thermoplastic resins, thermosetting resins, or rubbers having an elastic modulus of 1 to 1000 MPa can be given. In order to develop the film stretchability, rubbers are preferable. Examples of the rubbers include urethane rubber, acrylic rubber, silicone rubber, butadiene rubber, rubber containing a nitrile group such as nitrile rubber or hydrogenated nitrile rubber, isoprene rubber, vulcanized rubber, styrene-butadiene rubber, butyl rubber, chlorosulfonated polyethylene rubber, ethylene propylene rubber, vinylidene fluoride copolymer, and the like. Among these, rubber containing a nitrile group, chloroprene rubber, and chlorosulfonated polyethylene rubber are preferable, and rubber containing a nitrile group is particularly preferable. The elastic modulus in the present invention is preferably within a range of 3 to 600 MPa, more preferably 10 to 500 MPa, further preferably 30 to 300 MPa.

There is no particular limitation for the rubber containing a nitrile group as far as it is a rubber or elastomer containing a nitrile group, and nitrile rubber and hydrogenated nitrile rubber are preferable. Nitrile rubber is a copolymer of butadiene with acrylonitrile, and when the amount of bonding acrylonitrile increases, affinity with metal increases but rubber elasticity contributing to stretchability rather decreases. Therefore, the amount of bonding acrylonitrile in the acrylonitrile butadiene copolymer rubber is preferably 18 to 50% by mass, and more preferably 40 to 50% by mass.

There is no particular limitation for the rubber containing a nitrile group as far as it is a rubber or elastomer containing a nitrile group, and an acrylonitrile butadiene copolymer rubber that is a copolymer of butadiene with acrylonitrile is preferably given. As commercial products that may be used as the rubber containing a nitrile group, "Nipol (registered trademark) 1042" manufactured by Nippon Zeon, and the like are preferably given. The content of nitrile group in the rubber containing a nitrile group (in particular, the content of acrylonitrile in the acrylonitrile butadiene copolymer rubber) is preferably 18 to 50% by mass, and more preferably 28 to 41% by mass. When the content of bonding acrylonitrile in the acrylonitrile butadiene copolymer rubber increases, affinity to metal increases but the rubber elasticity contributing to the stretchability rather decreases.

Furthermore, the content of alkali metal in the flexible resin of the present invention is preferably 4000 ppm or less. By reducing the content of alkali metal, increase in viscosity with the passage of time due to pseudo crosslinkage of the conductive silver paste can be suppressed, and long-term storage stability is improved. Migration resistance of the formed conductive coat is also improved by reducing a metal ion source. Since the nitrile group having excellent affinity with silver powder preferentially adsorbs to the surface of the silver powder, the silver powder and the rubber containing a nitrile group in the coat do not become a fully homogeneous dispersed state, and uneven distribution or heterogeneity like a sea-island structure occurs. For this reason, even though the filling amount of the silver powder is small, an electrical conductivity network is easily formed. The rubber component increases by reducing the filling amount of the silver powder, whereby satisfactory elongation property and repetitive stretchability can be developed.

The flexible resin (c) in the present invention is contained in an amount of 7 to 35% by mass, preferably 9 to 28% by mass, and more preferably 12 to 20% by mass relative to the total amount of the conductive particles (a), the barium sulfate particles (b) and the flexible resin (c).

The content of the above-mentioned resin in the stretchable conductor layer (that is, the amount of the resin solid content in total solid matters in a conductive paste for forming a stretchable conductor layer) is preferably 55 to 85% by volume, and more preferably 60 to 80% by volume. If the content of the resin is too small, there is a tendency that the electrical conductivity may increase, but the stretchability may deteriorate. If the content of the resin is too large, there is a tendency that the stretchability may improve, but the electrical conductivity may decrease.

Furthermore, an epoxy resin may be blended to the conductive paste in the present invention. The epoxy resin in the present invention is preferably a bisphenol A type epoxy resin or a phenol novolac type epoxy resin. When blending an epoxy resin, a curing agent for the epoxy resin may be blended. As the curing agent, known amine compounds, polyamine compounds and the like can be used. The curing agent is preferably contained in an amount of 5 to 50% by mass, and more preferably 10 to 30% by mass relative to the epoxy resin. Moreover, the amount of the epoxy resin and the curing agent is 3 to 40% by mass, preferably 5 to 30% by mass, more preferably 8 to 24% by mass relative to the all resin components including the flexible resin.

The stretchable conductor layer in the present invention may contain an inorganic substance as long as the electrical conductivity and the stretchability are not impaired. As to the inorganic substance, there may be used various kinds of carbide such as silicon carbide, boron carbide, titanium carbide, zirconium carbide, hafnium carbide, vanadium carbide, tantalum carbide, niobium carbide, tungsten carbide, chromium carbide, molybdenum carbide, calcium carbide and diamond carbon lactam; various kinds of nitrides such as boron nitride, titanium nitride and zirconium nitride; various kinds of borides such as zirconium boride; various kinds of oxides such as titanium oxide (titania), calcium oxide, magnesium oxide, zinc oxide, copper oxide, aluminum oxide, silica, and colloidal silica; various kinds of titanate compounds such as calcium titanate, magnesium titanate, and strontium titanate; sulfides such as molybdenum disulfide; various kinds of fluorides such as magnesium fluoride and carbon fluoride; various kinds of metal soaps such as aluminum stearate, calcium stearate, zinc stearate, and magnesium stearate; and others such as talcum, bentonite, talc, calcium carbonate, bentonite, kaolin, glass fiber, and mica. When the inorganic substance as such is added, there may be cases where printing property and heat resistance in the formation of a stretchable conductor layer, and further, mechanical characteristics and durability for long time can be enhanced. Note that the inorganic substance may be used singly, or in combination of two or more thereof.

In the stretchable conductor layer in the present invention, if need arises, various kinds of additives such as thixotropic property imparting agent, antifoaming agent, flame retardant, tackifier, preventing agent for hydrolysis, leveling agent, plasticizer, antioxidant, ultraviolet absorber, flame retardant, pigment, and dye may be blended. Note that the additive may be used singly, or in combination of two or more thereof.

In the present invention, barium sulfate particles can be preferably contained. As the barium sulfate particles (b) in the present invention, ground barite obtainable by grinding a barite mineral called a natural barite, and a so-called precipitated barium sulfate produced by a chemical reaction can be used. It is preferred in the present invention to use the precipitated barium sulfate of which particle diameter is easily controlled. The average particle diameter of the barium sulfate particles preferably used, as determined by a dynamic light scattering method, is preferably 0.01 to 18 μm, more preferably 0.05 to 8 μm, and further preferably 0.2 to 3 μm. In addition, the barium sulfate particles in the present invention are preferably subjected to a surface treatment with the hydroxide and/or oxide of one or both of Al and Si. By such a surface treatment, the hydroxide and/or oxide of one or both of Al and Si adhere to the surface of the barium sulfate particles. The adhering amount of these compounds is preferably 0.5 to 50, and more preferably 2 to 30 relative to 100 of barium elements at an element ratio detected by X-ray fluorescence analysis.

The average particle diameter of the barium sulfate particles is preferably smaller than the average particle diameter of the conductive particles. The number average particle diameter of the conductive particles is preferably 1.5 times or more, further preferably 2.4 times or more, and still further preferably 4.5 times or more of the number average particle diameter of the barium sulfate particles. When the average particle diameter of the barium sulfate particles exceeds the above range, the irregularities on the surface of the resulting coat increase, which tends to cause a fracture of the coat when stretched. On the other hand, when the average particle diameter of the barium sulfate particles is smaller than the above range, the stretching durability enhancement effect is insufficient, the viscosity of the paste is increased, and as a result, it becomes difficult to manufacture the paste.

The barium sulfate particles in the present invention is contained in an amount of 2 to 30% by mass, preferably 3 to 20% by mass, and more preferably 4 to 15% by mass relative to the total amount of the conductive particles and the barium sulfate particles. If the amount of the barium sulfate particles exceeds the above range, the electrical conductivity of the surface of the resulting coat lowers. On the other hand, if the amount of the barium sulfate particles is less than the above range, the stretching durability enhancement effect tends to be hardly developed.

The stretchable conductor layer in the present invention can be formed in such a manner that a composition (conductive paste) where the above-mentioned ingredients are dissolved or dispersed in an appropriate organic solvent is directly applied to or printed on the first insulating layer in a desired pattern to form a coat, and then the organic solvent contained in the coat is evaporated and dried. Alternatively, it can be formed in such a manner that a conductive paste is applied to or printed on a release sheet or the like to form a coat, the organic solvent contained in the coat is then evaporated and dried to form a sheet-like stretchable conductor layer in advance, the sheet-like stretchable conductor layer is cut out or punched out in a desired pattern, and the resulting layer is stacked on the first insulating layer.

In the present invention, a paste for forming a stretchable conductor contains a solvent (d). The solvent in the present invention is water or an organic solvent.

The content of the solvent is not particularly limited since it should be appropriately investigated depending on the viscosity required of the paste, and it is generally preferred to be 30 to 80 in a mass ratio when the total mass of the conductive particles (a), the barium sulfate particles (b) and the flexible resin (c) is defined as 100.

As to the organic solvent used in the present invention, its boiling point is preferred to be equal to or higher than 100° C. and lower than 300° C., and more preferred to be equal to or higher than 130° C. and lower than 280° C. When the boiling point of the organic solvent is too low, the solvent may be evaporated during the paste production process and during use of the paste, and there is concern that the ratio of the ingredients constituting the conductive paste will be apt to change. On the other hand, when the boiling point of the organic solvent is too high, the amount of solvent remaining in the dried and cured coat becomes large, and hence there is concern that reliability of the coat will deteriorate.

Specific examples of the organic solvent using in the present invention include cyclohexanone, toluene, xylene, isophorone, γ-butyrolactone, benzyl alcohol, Solvesso 100, 150 and 200 (manufactured by Exxon Chemical), propylene glycol monomethyl ether acetate, terpineol, butyl glycol acetate, diamylbenzene (boiling point: 260 to 280° C.), triamylbenzene (boiling point: 300 to 320° C.), n-dodecanol (boiling point: 255 to 259° C.), diethylene glycol (boiling point: 245° C.) ethylene glycol monoethyl ether acetate (boiling point: 145° C.), diethylene glycol monoethyl ether acetate (boiling point: 217° C.), diethylene glycol monobutyl ether acetate (boiling point: 247° C.), diethylene glycol dibutyl ether (boiling point: 255° C.), diethylene glycol monoacetate (boiling point: 250° C.), triethylene glycol diacetate (boiling point: 300° C.), triethylene glycol (boiling point: 276° C.), triethylene glycol monomethyl ether (boiling point: 249° C.), triethylene glycol monoethyl ether (boiling point: 256° C.), triethylene glycol monobutyl ether (boiling point: 271° C.), tetraethylene glycol (boiling point: 327° C.), tetraethylene glycol monobutyl ether (boiling point: 304° C.), tripropylene glycol (boiling point: 267° C.), tripropylene glycol monomethyl ether (boiling point: 243° C.), and 2,2,4-trimethyl-1,3-pentanediol monoisobutyrate (boiling point: 253° C.). As to a petroleum hydrocarbon, there may be exemplified AF Solvent No. 4 (boiling point: 240 to 265° C.), No. 5 (boiling point: 275 to 306° C.), No. 6 (boiling point: 296 to 317° C.), and No. 7 (boiling point: 259 to 282° C.), and No. 0 Solvent H (boiling point: 245 to 265° C.) manufactured by Nippon Oil Corporation. Note that the organic solvent may be used singly, or in combination of two or more thereof. Such organic solvents are appropriately contained such that a conductive silver paste has a viscosity suitable for printing or the like.

The paste for forming a stretchable conductor in the present invention can be prepared by mixing and dispersing the conductive particles (a), the barium sulfate particles (b), the stretchable resin (c) and the solvent (d) as materials with a disperser such as a dissolver, three-roll mill, rotation/revolution mixer, attritor, ball mill, sand mill or the like.

Into the paste for forming a stretchable conductor in the present invention, a known organic or inorganic additive such as a printability imparting agent, color tone adjusting agent, leveling agent, antioxidant, ultraviolet absorber, or the like can be blended as long as the contents of the invention are not impaired.

In the present invention, by printing an electrical wiring directly on a fabric using the above-mentioned paste for forming a stretchable conductor, a garment having a wiring composed of a stretchable conductor composition can be produced. As a printing method, a screen printing method, a lithographic offset printing method, a paste-jet method, a flexographic printing method, a gravure printing method, a gravure offset printing method, a stamping method, a stencil method, or the like may be used. In the present invention, it is preferred to use a screen printing method or a stencil method. A method to directly draw a wiring using a dispenser or the like may also be interpreted as a printing in a broad sense.

After forming the coat from the conductive paste, in order to evaporate and dry the organic solvent, heating may be carried out under ambient air, under vacuum atmosphere, under inert gas atmosphere, under reductive gas atmosphere, etc. Heating temperature is, for example, within a temperature range of 20 to 200° C., and it can be selected by taking the demanded electrical conductivity, the heat resistance of the substrate or the insulating layer, etc. into consideration.

The dry thickness of the stretchable conductor layer is preferably 150 to 40 μm, and more preferably 100 to 50 μm. If the stretchable conductor layer is too thin, it may easily deteriorate by repeated stretching of the stretchable electrode sheet and the stretchable wiring sheet, and there is a possibility of inhibition or blocking of electrical conductivity. On the other hand, if the stretchable conductor layer is too thick, the stretchability of the substrate may be inhibited, and wear comfort may be inhibited since the thickness of the entire electrode and wiring increases.

<Second Insulating Layer>

In the stretchable wiring sheet of the present invention, a second insulating layer is formed on the above-mentioned stretchable conductor layer. Thus, when a biological information measurement interface produced using the stretchable wiring sheet is worn, moisture such as rain or perspiration or the like is prevented from contacting the stretchable conductor layer.

As examples of the resin forming the second insulating layer, the same resins as those exemplified above for the resin forming the first insulating layer can be given, and the same applies to the preferred resins. The resin forming the second insulating layer may be also used singly, or in combination of two or more thereof. The resin forming the first insulating layer and the resin forming the second insulating layer may be the same or may be different. However, it is preferred that they be the same in respect of the coverage of the stretchable conductor layer and in respect of reducing the damage of the stretchable conductor layer due to uneven stress at the time of stretching of the wiring sheet. The second insulating layer can be formed in the same manner as in the first insulating layer as described above. It is also possible to use a commercially available sheet or film having an appropriate physical properties as described later.

The thickness of the second insulating layer is preferably 5 to 150 μm, more preferably 10 to 70 μm, and further preferably 20 to 50 μm. If the second insulating layer is too thin, it is apt to deteriorate due to the repeated stretching of the substrate, and the insulating effect becomes insufficient. On the other hand, if the second insulating layer is too thick, the stretchability of the wiring sheet may be inhibited, and wearing feeling may deteriorate since the thickness of the entire wiring increases.

<Features of Stretchable Electrode Sheet and Stretchable Wiring Sheet>

In the stretchable electrode sheet and the stretchable wiring sheet of the present invention, the above-mentioned stretchable conductor layer has an electric resistance of 300 Ω/cm or less, preferably 200 Ω/cm or less, and more preferably 100 Ω/cm or less. Still further, 10 Ω/cm is preferable, 1 Ω/cm is preferable, 0.1 Ω/cm is preferable, and 0.01 Ω/cm is preferable. The resistance value of the conductor layer of the stretchable electrode sheet and the stretchable wiring sheet of the present invention is also called a wiring resistance and indicates a resistance value per length of 1 cm when a 1 cm-wide-conductor is formed, and in this case, it equals a so-called sheet resistance.

The electric resistance of the conventional conductive fabric is around 1,000 Ω/cm, whereas the stretchable conductor layer of the stretchable electrode sheet and the stretchable wiring sheet of the present invention is formed of a conductive filler that is mainly composed of metal powder, and a rubber containing a sulfur atom and/or a rubber containing a nitrile group as a resin, and therefore exhibits the feature that the electric resistance of the stretchable conductor layer can be kept to 300 Ω/cm or less. The details of the electric resistance measurement in the present invention are described in the Examples.

In a preferred embodiment of the stretchable electrode sheet and the stretchable wiring sheet of the present invention, a load applied when stretching at a stretching rate of 10% is 100 N or less, more preferably 80 N or less, and further preferably 50 N or less. In the conventional conductive fabric or wiring, a load applied when stretching at a stretching rate of 10% is 100 N or more, and it is difficult to follow the elongation of the substrate, which has caused an inhibition of wear comfort when being worn. In contrast, by preferably using the rubber containing a sulfur atom and/or the rubber containing a nitrile group as a resin for forming the stretchable conductor layer, and by further using a flexible resin having an elastic modulus of 1 to 1000 MPa, preferably 3 to 600 MPa, more preferably 10 to 500 MPa, and further preferably 30 to 300 MPa, the stretchable electrode sheet and the stretchable wiring sheet of the present invention exhibit the feature that a load applied when stretching at a stretching rate of 10% can be suppressed to 100 N or less. The details of the above-mentioned stretching-load test in the present invention are described in the Examples.

In a preferred embodiment of the stretchable electrode sheet and the stretchable wiring sheet of the present invention, the change in electric resistance at 20% stretching is 5-fold or less, more preferably 4-fold or less, and further preferably 3-fold or less. The conventional conductive fabric or wiring may be usually broken in a stage before the stretching rate reaches 20%, or even if it can be stretched up to a stretching rate of 20%, the electrical conductivity significantly decreases to such an extent that the resistance change ratio exceeds 10-fold. In contrast, by preferably using the rubber containing a sulfur atom and/or the rubber containing a nitrile group as a resin for forming the stretchable conductor layer, and by further using a flexible resin having an elastic modulus of 1 to 1000 MPa, preferably 3 to 600 MPa, more preferably 10 to 500 MPa, and further preferably 30 to 300 MPa, the stretchable electrode sheet and the stretchable wiring sheet of the present invention exhibit the feature that the resistance change ratio can be suppressed to 5-fold or less even when stretched up to a stretching rate of 20%. The details of the above-mentioned stretching test in the present invention are described in the Examples.

In a preferred embodiment of the stretchable electrode sheet and the stretchable wiring sheet of the present invention, the stretchable electrode sheet and the stretchable wiring sheet have a thickness of 200 μm or less, more preferably 180 μm or less, and further preferably 150 μm or less. The conventional conductive fabric or wiring has a thickness of 200 μm or more and tends to give a wearer the sensation of a foreign object when it contacts the wearer's skin. In contrast, the stretchable electrode sheet and the stretchable wiring sheet of the present invention exhibit the feature that the thickness can be suppressed to 200 μm or less while having a high electrical conductivity since the conductor layer is formed of the conductive filler that is mainly composed of metal powder and the rubber containing a sulfur atom and/or the rubber containing a nitrile group as a resin.

The stretchable electrode sheet and the stretchable wiring sheet of the present invention may be laminated on a substrate described later. It is preferred to be laminated on the insulating first layer side to the substrate, and a lamination method is not particularly limited as long as it is a conventionally known lamination method such as a lamination with an adhesive, a lamination by hot pressing, or the like. However, from the viewpoint of fittability to human bodies and followability at the time of exercise or action while wearing to measure biological information, a lamination method that does not prevent the stretchability of the electrode and the wiring sheet is preferred.

<Biological Information Measurement Interface>

The biological information measurement interface of the present invention has a configuration in which the stretchable electrode sheet and the stretchable wiring sheet of the present invention are laminated on a substrate. The substrate of the biological information measurement interface of the present invention is not particularly limited as long as it is a strip-shaped material such as a belt, a brassiere or the like to be attached at least in a circumferential direction of a trunk of a human body and/or a garment made of a woven or knitted fabric or a non-woven fabric. Conventionally known products composed of various resins, or a woven or knitted fabric or a nonwoven fabric composed of natural fibers, synthetic fibers, or semi-synthetic fibers can be used. However, from the viewpoint of fittability to human bodies and followability at the time of exercise or action while wearing to measure biological information, a substrate having stretchability is preferred. Such a biological information measurement interface serves as means for measuring biological information of a wearer, and has a usual method for wearing and a usual wear feeling. Therefore, a user can easily measure various biological information by just wearing it.

EXAMPLES

Hereinafter, the present invention will be described more in detail by way of examples, and the present invention is not limited to the following examples. Of course, the present invention can be carried out while changes are appropriately made without departing from the spirit of the foregoing and following descriptions, and these change are all encompassed in the technical scope of the present invention.

Resins for forming insulating layers and conductive pastes used in the following Examples and Comparative Examples were prepared as described below.

[Conductive Paste]

A resin shown in Table 1 was dissolved in diethylene glycol monomethyl ether acetate to prepare a solution. To this solution, a liquid wherein silver particles ("Aggregated silver powder G-35" manufactured by DOWA Electronics, average particle diameter: 5.9 μm) and a surface-treated carbon nanotube (CNT) prepared as necessary by a method described later were uniformly dispersed was added such that the ingredients were compounded at a ratio shown in Table 1, and was then kneaded using a three-roll mill to obtain a conductive paste.

Details of resins shown in Table 1 are as follows.
Nitrile group-containing rubber: "Nipol (registered trademark) 1042" (content of acrylonitrile: 33.3% by mass) manufactured by Nippon Zeon
Sulfur-containing rubber: "Thiokol (registered trademark) LP-23" (content of sulfur: 21.5% by mass) manufactured by Toray Fine Chemical
Polyester: "Vylon (registered trademark) RV630" manufactured by Toyobo The surface-treated carbon nanotube (CNT) was prepared by the following method.

[Preparation of CNT Having Acrylonitrile Butadiene Oligomer on its Surface]

50 mg of a multi-wall carbon nanotube (SWeNT MW100, manufactured by South West Nano Technologies; diameter: 6 to 9 nm; length: 5 μm; aspect ratio: 556 to 833) was added to 100 ml of a 0.006 mol/l ethanolic solution of o-phenylphenyl glycidyl ether and subjected to an ultrasonic treatment for 30 minutes. After filtering through a PTFE membrane, washing with ethanol was carried out for several times followed by drying to prepare a carbon nanotube having a glycidyl group on its surface.

Next, the resulting carbon nanotube was added to a tetrahydrofuran solution of Hypro™ 1300×16ATBN, which is an acrylonitrile butadiene oligomer having a terminal amino group (content of acrylonitrile: 18% by mass; amine equivalent: 900; manufactured by Emerald Performance Materials), and subjected to a dispersion treatment for 30 minutes using an ultrasonic treating machine. Furthermore, the resulting solution was heated to 60° C. and subjected to an ultrasonic treatment for one hour, and after filtering through a PTFE membrane, washing with tetrahydrofuran was carried out for several times followed by drying to obtain a carbon nanotube having an acrylonitrile butadiene oligomer on its surface.

[Resin for Forming Insulating Layers]

To 9 parts by mass of resin shown in Table 1, 4 parts by mass of a mixture of 1 part by mass of thickener ("ACTGEL AP200" manufactured by Senka, acrylic acid based polymer) and 10 parts by mass of water was added to obtain a resin for forming an insulating layer.

Details of resins shown in Table 1 are as follows.
Polyurethane A: "UREARNO (registered trademark) W600" manufactured by Arakawa Chemical Industries (polyester-based anionic aqueous polyurethane, content of urethane resin: 35% by mass, isopropyl alcohol: 5% by mass)
Polyurethane B: "UREARNO (registered trademark) W321" manufactured by Arakawa Chemical Industries (polyester-based anionic aqueous polyurethane, content of urethane resin: 35% by mass, isopropyl alcohol: 9% by mass)

A conductive paste prepared in accordance with the compounding ratio shown in Table 1 was applied onto a release sheet and dried in a hot-air drying oven of 120° C. for 30 minutes or longer to produce a sheet-like stretchable conductor layer with the release sheet.

Next, a resin for forming an insulating layer shown in Table 1 was applied to a region having a length of 15 cm and a width of 3 cm on a release sheet, and on this region, the stretchable conductor layer obtained by cutting out the above-mentioned sheet-like stretchable conductor layer with the release sheet into a length of 15 cm and a width of 1 cm and then peeling off the release sheet was laminated. Subsequently, drying was performed in a hot-air drying oven of 100° C. for 20 minutes to form a first insulating layer and a stretchable conductor layer, thereby to obtain a stretchable electrode sheet.

Incidentally, a resin for forming an insulating layer used as the first insulating layer was applied, dried in a hot-air drying oven of 100° C. for 20 minutes, and then peeled off from the release sheet to obtain an insulating sheet, and when this insulating sheet was compared with the stretchable conductor layer sheet similarly peeled off from the release sheet with respect to a load when stretched at a stretching load of 10%, the load of the insulating sheet was larger than the load of the stretchable conductor layer sheet.

Next, to a region having a length of 10 cm and a width of 3 cm enough to cover the laminated stretchable conductor layer, the same resin for forming an insulating layer as the resin that was used for forming the above-mentioned first insulating layer was applied and dried in a hot-air drying oven of 100° C. for 20 minutes or longer to form a second insulating layer on the stretchable conductor layer, thereby to obtain a stretchable wiring sheet having a configuration of first insulating layer/stretchable conductor layer/second insulating layer.

Each of the stretchable electrodes and wiring sheets obtained in Examples and Comparative Examples was subjected to the following tests and evaluated.

<Measurement of Electric Resistance>

For the surface of the stretchable electrode sheet and the stretchable wiring sheet obtained by the above-mentioned formation method, a resistance value (Ω) per measurement distance of 1 cm in a conductor pattern having a width of 1 cm was measured using Digital Multimeter ("YOKOGAWA TY530" manufactured by Yokogawa Meters & Instruments).

<Stretching-Load Test>

Using Tensilon ("RTM-250" manufactured by Orientec Corporation), loads (N) applied when the stretchable electrode sheet and the stretchable wiring sheet, insulating layer sheet, stretchable conductor sheet, or the like having a width of 3 cm and a test length of 5 cm were stretched at 10% stretching (displacement amount: 0.5 cm) were measured.

<Stretching Test>

Using a stretch tester (a hand-rotated drawer) provided with two chucks having a width of 2.5 cm, the stretchable electrode or wiring sheet was held with a distance of 5 cm between the chucks and stretched by a stretching rate of 20% (displacement amount: 1 cm) in the longitudinal direction. Using Digital Multimeter ("YOKOGAWA TY530" manufactured by Yokogawa Meters & Instruments), resistance values (Ω) before and after the test were measured at outer sides of opposite two chucks (measurement distance: 10 cm). The measurement of resistance values was conducted immediately after stretching (within three seconds).

<Resistance Change Ratio>

The resistance change ratio is a ratio of a resistance value ($R_{20}$) at a stretching rate of 20% to a resistance value ($R_0$) at a stretching rate of 0% (before the test) (that is, resistance change ratio=$R_{20}/R_0$ (fold)).

Hereinafter, the invention will be explained in more detail and specifically by further showing Examples. Evaluation items newly required in the following Examples were measured by the following method.

<Amount of Nitrile>

The amount of nitrile was converted from the composition ratio obtained by analyzing the resulting resin material by NMR to a ratio by mass (% by mass) of monomer.

<Mooney Viscosity>

The measurement was conducted using SMV-300RT "Mooney Viscometer" manufactured by Shimadzu Corporation.

<Amount of Alkali Metal>

The resin was subjected to an ashing treatment, the resulting ash was extracted by means of hydrochloric acid, the contents of sodium and potassium were determined by atomic absorption spectrometry, and both contents were summed.

TABLE 1

| | | | Example 1 | Example 2 | Example 3 | Example 4 | Example 5 | Example 6 | Example 7 | Example 8 |
|---|---|---|---|---|---|---|---|---|---|---|
| Conductor layer | Classification | | Electrode | Wiring | Electrode | Wiring | Wiring | Wiring | Wiring | Electrode |
| | Conductive filler (% by volume) | Silver particles | 30 | 30 | 30 | 30 | 27 | 30 | 30 | 30 |
| | | CNT | — | — | 5 | 5 | 3 | — | — | — |
| | Resin (% by volume) | Nitrile group-containing rubber | 70 | 70 | 65 | 65 | 70 | 70 | 70 | — |
| | | Sulfur-containing rubber | — | — | — | — | — | — | — | 70 |
| | | Polyester | — | — | — | — | — | — | — | — |
| | Thickness (μm) | | 60 | 60 | 60 | 60 | 60 | 120 | 60 | 60 |
| first/second insulating layer | Polyurethane A | | 35/— | 35/35 | 35/— | 35/35 | 35/35 | 35/35 | 60/60 | 35/— |
| | Polyurethane B | | — | — | — | — | — | — | — | — |
| Total thickness (μm) | | | 95 | 130 | 95 | 130 | 130 | 190 | 180 | 95 |
| Wiring resistance (Ω/cm) | | | 83 | 84 | 65 | 67 | 77 | 81 | 84 | 100 |
| Load at stretching of a stretching rate of 10% (N) | | | 24 | 46 | 31 | 52 | 42 | 85 | 93 | 20 |
| Resistance change ratio at 20% stretching (fold) | | | 3.3 | 2.5 | 2.1 | 1.8 | 3 | 2.7 | 3.6 | 4.2 |

| | | | Example 9 | Example 10 | Example 11 | Comparative Example 1 | Comparative Example 2 | Comparative Example 3 | Comparative Example 4 |
|---|---|---|---|---|---|---|---|---|---|
| Conductor layer | Classification | | Wiring | Electrode | Wiring | Wiring | Wiring | Wiring | Wiring |
| | Conductive filler (% by volume) | Silver particles | 30 | 30 | 30 | 30 | 10 | 30 | 30 |
| | | CNT | — | — | — | — | — | — | — |
| | Resin (% by volume) | Nitrile group-containing rubber | — | 70 | 70 | — | 90 | 70 | 70 |
| | | Sulfur-containing rubber | 70 | — | — | — | — | — | — |
| | | Polyester | — | — | — | 70 | — | — | — |
| | Thickness (μm) | | 60 | 60 | 60 | 60 | 60 | 100 | 200 |
| first/second insulating layer | Polyurethane A | | 35/35 | — | — | 35/35 | 35/35 | 100/100 | 35/35 |
| | Polyurethane B | | — | 35/— | 35/35 | — | — | — | — |
| Total thickness (μm) | | | 130 | 95 | 130 | 130 | 130 | 300 | 270 |
| Wiring resistance (Ω/cm) | | | 121 | 85 | 85 | 158 | 1455 | 92 | 71 |
| Load at stretching of a stretching rate of 10% (N) | | | 37 | 59 | 82 | 216 | 40 | 422 | 265 |
| Resistance change ratio at 20% stretching (fold) | | | 3.8 | 2.9 | 2.9 | (breaking of wiring) | 7.7 | 3.6 | 4.4 |

<Elastic Modulus>

The resin material was heated, compressed and molded into a sheet having a thickness of 200±20 µm, and then punched out into a dumbbell shape defined by ISO 527-2-1A to obtain a test piece. A tensile test was performed by the method defined in ISO 527-1 to determine an elastic modulus.

<Repeated Stretching Durability of Resin Material>

(1) Formation of Test Piece Sheet

A resin material was heated, compressed and molded into a sheet having a thickness of 200±20 µm and then punched out into a dumbbell shape defined by ISO 527-2-1A to obtain a test piece.

(2) Stretching Test

An IPC bending tester manufactured by Yamashita Materials Corporation was modified, a reciprocating stroke of the tester was set to 13.2 mm, the test piece was fixed on a movable plate side with a clamp, the other end of the test piece was fixed to another fixed end with a clamp, and using a portion having a width of 10 mm and a length 80 mm in the dumbbell-shaped test piece, an effective length was adjusted to be 66 mm (corresponding to 20% elongation). Using the apparatus modified to enable a sample to be repeatedly stretched, stretching of the test piece was repeatedly performed 5000 times, and the durability to repeated stretching was evaluated by comparing the appearances before and after the test. A case where no change was found in the appearance as compared with the initial appearance was evaluated as "good", a case where cracks or the like were observed on the resin surface was evaluated as "poor".

<Repeated Stretching Durability of Conductive Paste>

A paste for forming a stretchable conductor was printed onto a sheet having a thickness of 200±20 µm obtained from a stretchable resin R1 as a substrate by screen printing to form a rectangular pattern of 180 mm×30 mm having a dry thickness of 30 µm, and dried and cured at 120° C. for 30 minutes. Next, the rectangular pattern portion was punched out into a dumbbell shape defined by ISO 527-2-1A to obtain a test piece.

An IPC bending tester manufactured by Yamashita Materials Corporation was modified, a reciprocating stroke of the tester was set to 13.2 mm, the test piece was fixed on a movable plate side with a clamp, the other end of the test piece was fixed to another fixed end with a clamp, and using a portion having a width of 10 mm and a length 80 mm in the dumbbell-shaped test piece, an effective length was adjusted to be 66 mm (corresponding to 20% elongation). Using the apparatus modified to enable a sample to be repeatedly stretched, the sample was clipped with metal clips on portions wrapped with aluminum foil at 0 to 5 mm outside from both ends of the stretching effective length of 66 mm, and was repeatedly stretched while monitoring resistance values with the tester. The resistance values were read every 10 times until repeated stretching of 600 times, and in stretchings of more than 600 times, stretching was stopped every 50 times in a state of a stretching rate of 0%, a value after one minute after the stop was read and recorded, the number of times at the time when the resistance value had reached 100-fold of the initial value was recorded, and then the test was aborted.

<Electrical Conductivity (Sheet Resistance, Specific Resistance)>

The resistance value [Ω] of a part having a width of 10 mm and a length of 80 mm in the central portion of a dumbbell-shaped test piece defined by ISO 527-2-1A was measured using Milliohmmeter manufactured by Agilent Technologies, and a sheet resistance value "Ω square" was obtained by multiplying the measured resistance value by the aspect ratio (⅛) of the test piece.

Furthermore, by multiplying the resistance value [Ω] by a cross-sectional area (width of 1 [cm] mm×thickness [cm]) and then dividing by the length (8 cm), a specific resistance [Ωcm] was determined.

<Evaluation of Migration Resistance>

Using the conductive paste, a test pattern in which two conductor patterns having a width of 1.0 mm and a length of 30.0 mm were parallel at intervals of 1.0 mm was printed on a polyester film by screen printing, and cured to obtain a test piece: in a state where DC5V was applied between the electrodes of the test piece, deionized water was added dropwise between the conductors, and the time taken until the electrodes were short-circuited by dendritic precipitates was measured, and a case where the time was within 60 seconds was evaluated as "poor" and a case where the time was 60 seconds or longer was evaluated as "good". Note that the dropwise amount of deionized water was adjusted to an amount enough that water droplets cover in a width of 8 to 10 mm between the electrodes, and determination of short circuit was performed through visual observation.

<Surface Feeling>

Ten adults including five men and five women served as subjects, the printed surface was brought into contact with the skin of the abdomen of each of the subjects, and the sensory evaluation of texture was performed according to 5 grades from 5 points as "good feeling" to 1 point as "bad feeling". Averaging points of ten persons, a case of 4 or more points was evaluated as "very good", a case of 3 or more and less than 4 points was evaluated as "good", a case of 2 or more and less than 3 points was evaluated as "fair", a case of less than 2 points was evaluated as "poor".

<Average Particle Diameter>

The measurement was performed using a dynamic light-scattering particle size distribution analyzer LB-500 manufactured by Horiba, Ltd.

<Composition Analysis of Inorganic Particles>

Composition of inorganic particles to be used was analyzed using an X-ray fluorescence analyzer (X-ray fluorescence analyzer system 3270, manufactured by Rigaku Corporation) to examine Al components and Si components. Note that the amounts of coated Al and Si were obtained by converting the detected amount of metallic compounds of the Al components and the Si components into the amounts of the corresponding oxides (namely, Al components were calculated as Al2O3, Si components were calculated as SiO2).

<Wiring Resistance>

The resulting conductive paste was applied onto a release sheet with a bar coater and dried in a hot-air drying oven of 120° C. for 30 minutes or longer. The similar operation was repeated as necessary such that the thickness of the stretchable conductor layer became 70 µm to produce a sheet-like stretchable conductor layer with a release sheet.

Next, the resin for forming an insulating layer shown in Table 1 was applied to a region having a length of 15 cm and a width of 3 cm on a release sheet, and on this region, the stretchable conductor layer obtained by cutting out the above-mentioned sheet-like stretchable conductor layer with the release sheet into a length of 15 cm and a width of 1 cm and then peeling off the release sheet was laminated. Subsequently, drying was performed in a hot-air drying oven of 100° C. for 20 minutes to form a first insulating layer and a stretchable conductor layer, thereby to obtain a stretchable electrode sheet.

Next, to a region having a length of 10 cm and a width of 3 cm enough to cover the laminated stretchable conductor layer, the same resin for forming an insulating layer as the resin that was used for forming the above-mentioned first insulating layer was applied and dried in a hot-air drying oven of 100° C. for 20 minutes or longer to form a second insulating layer on the stretchable conductor layer, thereby to obtain a test piece of a stretchable wiring sheet having a configuration of first insulating layer/stretchable conductor layer/second insulating layer. The wiring resistance (resistance value per length of 1 cm in the conductor width of 1 cm) of the resulting stretchable wiring sheet was determined in the same manner as in Examples 1 to 11.

<Load at 10% Stretching>

Using the obtained test piece, the measurement was performed in the same manner as in Example 1.

<Resistance Ratio at 20% Stretching>

Using the obtained test piece, the measurement was performed in the same manner as in Example 1.

Production Example

<Polymerization of Synthetic Rubber Material>

The following materials were put into a stainless steel reactor equipped with a stirrer and a water cooling jacket and gently stirred while keeping the bath temperature at 15° C. by flowing nitrogen.

| butadiene | 54 parts by mass |
| acrylonitrile | 46 parts by mass |
| deionized water | 270 parts by mass |
| sodium dodecylbenzenesulfonate | 0.5 part by mass |
| sodium naphthalenesulfonate condensate | 2.5 parts by mass |
| t-dodecyl mercaptan | 0.3 part by mass |
| triethanolamine | 0.2 part by mass |
| sodium carbonate | 0.1 part by mass |

Next, an aqueous solution prepared by dissolving 0.3 part by mass of potassium persulfate in 19.7 parts by mass of deionized water was added dropwise into the reactor over 30 minutes, reaction was further continued for 20 hours, an aqueous solution prepared by dissolving 0.5 part by mass of hydroquinone in 19.5 parts by mass of deionized water was then added thereto, and an operation for stopping the polymerization reaction was carried out.

Next, in order to distill off unreacted monomers, the pressure in the reactor was first reduced, and then steam was introduced into the reactor to recover the unreacted monomers, thereby to obtain a synthetic rubber latex (L1) composed of NBR.

Sodium chloride and dilute sulfuric acid were added to the obtained latex, aggregation and filtration were performed. Then, deionized water in an amount 20 times in volume ratio to the resin was divided in five portions, the resin was washed by repeating redispersion in the deionized water and filtration, and dried in air to obtain a synthetic rubber resin R1.

The evaluation results of the obtained synthetic rubber resin R1 are shown in Table 1. The operations were similarly performed by changing raw materials, polymerization conditions, washing conditions, and the like to obtain resin materials R2 to R6 shown in Table 2. Abbreviations in the table are as follows:

NBR: acrylonitrile butadiene rubber
NBIR: acrylonitrile-isoprene rubber (isoprene: 10% by mass)
SBR: styrene-butadiene rubber (styrene/butadiene=50/50% by mass)

TABLE 2

| Latex | L1 | L2 | L3 | L4 | L5 | L6 |
| Stretchable resin | R1 | R2 | R3 | R4 | R5 | R6 |
| Ingredient | NBR | NBR | NBIR | SBR | NBR | NBR |
| --- | --- | --- | --- | --- | --- | --- |
| Polymerization temperature | 15 | 12 | 15 | 20 | 50 | 15 |
| Amount of nitrile [% by mass] | 43 | 35 | 26 | 0 | 39 | 42 |
| Amount of alkali metal [ppm] | 42 | 62 | 47 | 53 | 48 | 5600 |
| Mooney viscosity | 53 | 42 | 34 | 64 | 70 | 52 |
| Elastic modulus MPa | 31 | 25 | 21 | 63 | 147 | 33 |
| Washing | yes | yes | yes | yes | yes | no |
| Repeated stretching durability | good | good | good | good | good | good |

Preparation of Barium Sulfate Particles (A)

Warman Pump (inlet diameter: 40 mm, outlet diameter: 25 mm, internal volume: 850 mL, impeller rotation speed: 2380 rpm) was used as a reaction vessel. A sulfuric acid aqueous solution with a concentration of 110 g/L (1.1 mol/L) and a temperature of 30° C. was allowed to be sucked into this pump at a constant flow rate of 700 L/h. Simultaneously, a barium sulfide aqueous solution with a concentration of 120 g/L (0.71 mol/L) and a temperature of 50° C. was allowed to be sucked into the pump at a constant rate of 600 L/h to prepare 1000 mL of aqueous slurry (solid content: 95 g/L), and the slurry was heated to 60° C. Sodium silicate in an amount corresponding to 4.0 g of $SiO_2$ was diluted with 100 mL of pure water, and the mixture was added dropwise to the slurry over 20 minutes. Then, sodium aluminate in an amount corresponding to 2.0 g of $Al_2O_3$ was diluted with 100 mL of pure water and added dropwise to the slurry over 20 minutes. The reaction system was further heated to 70° C., and after stirring for 30 minutes, the slurry was neutralized with diluted sulfuric acid to pH 8 over 30 minutes. After further stirring for 10 minutes, the slurry was filtrated. The separated cake was washed thoroughly with water, and dried to give dried chips. The chips were crushed roughly, and then pulverized with an air current pulverizer. The obtained powder had a coated amount corresponding to 3.5% by mass of $SiO_2$ and 1.7% by mass of $Al_2O_3$ relative to the total amount of ultrafine barium sulfate particles that are base particles, and coated substances, and had the average particle diameter measured by a dynamic light scattering method of 0.3 μm.

Preparation of Barium Sulfate Particles (B)

Precipitated barium sulfate TS-1 manufactured by Takehara Kagaku Kogyo was used as barium sulfate particles (B). As a result of analyzing in the same manner as in the preparation of barium sulfate (A), the content of $SiO_2$ was 0.1% or less, and the content of $Al_2O_3$ was 0.1% or less. Therefore, these were judged not to be substantially contained. The average particle diameter determined by the same method was 0.6 μm.

Preparation of Barium Sulfate Particles (C)

Ground barite W-1 manufactured by Takehara Kagaku Kogyo was used as barium sulfate particles (C). The content of $SiO_2$ was 0.3% by mass, and the content of $Al_2O_3$ was 0.2% by mass. These were all judged as impurities because ground barite is derived from a natural product. The average particle diameter determined by the same method was 1.7 μm.

Titanium Oxide Particles (D)

Titanium oxide particles R-38L manufactured by Sakai Chemical Industry were used as titanium oxide particles (D).

The average particle diameter was 0.4 μm. A list of the above-mentioned barium sulfate particles and titanium oxide particles is shown in Table 2.

TABLE 3

|  | Inorganic particles | | | |
|---|---|---|---|---|
|  | A barium sulfate | B barium sulfate | C barium sulfate | D titanium oxide |
| Particle diameter [μm] | 0.3 | 0.6 | 1.7 | 0.4 |
| Amount of $SiO_2$ % by mass covering (detectable amount) | 3.5 | <0.1 | 0.3 | no analysis |
| Amount of $Al_2O_3$ % by mass covering (detectable amount) | 1.7 | <0.1 | 0.2 | no analysis |

[Preparation of Conductive Paste]

1.5 parts by mass of a liquid bisphenol-A based epoxy resin with an epoxy equivalent of 175 to 195, 10 parts by mass of the stretchable resin (R1) obtained in the production example, and 0.5 part by mass of the latent curing agent [trade name: Amicure PN23 manufactured by Ajinomoto Fine Chemical Co., Ltd.] were mixed and stirred with 30 parts by mass of isophorone to be dissolved, thereby to obtain a binder resin composition A1. Next, 58.0 parts by mass of fine flaky silver powder [trade name: Ag-XF301 manufactured by Fukuda Metal Foil & Powder Co., Ltd.] having an average particle diameter of 6 μm was added to the binder resin composition A1, uniformly mixed and dispersed by a three-roll mill to obtain a conductive paste C1. The evaluation results of the obtained conductive paste C1 are shown in Table 4-1.

Then, blending was carried out by changing the materials to obtain conductive pastes C2 to C16 as shown in Table 4-1 and Table 4-2. Likewise, the evaluation results are shown in Table 4-1 and Table 4-2.

Note that in Table 4-1 and Table 4-1, amorphous silver 1 is an aggregated silver powder G-35 (average particle diameter: 5.9 μm) manufactured by DOWA Electronics, and amorphous silver 2 is an aggregated silver powder (average particle diameter: 2.1 μm) obtained by wet-classifying the aggregated silver powder G-35 manufactured by DOWA Electronics.

TABLE 4-1

| | Conductive paste | | Example 12 C1 | Example 13 C2 | Example 14 C3 | Example 15 C4 | Example 16 C5 | Example 17 C6 | Example 18 C7 | Example 19 C8 |
|---|---|---|---|---|---|---|---|---|---|---|
| Compounded composition | Epoxy resin | parts by mass | 1.5 | — | 1.5 | — | — | — | — | 1.5 |
| | Stretchable resin (R1) | parts by mass | 10.0 | — | — | — | — | 12.0 | 12.0 | 10.0 |
| | Stretchable resin (R2) | parts by mass | — | 12.0 | — | — | — | — | — | — |
| | Stretchable resin (R3) | parts by mass | — | — | 10.0 | — | — | — | — | — |
| | Stretchable resin (R4) | parts by mass | — | — | — | 12.0 | — | — | — | — |
| | Stretchable resin (R5) | parts by mass | — | — | — | — | 12.0 | — | — | — |
| | Stretchable resin (R6) | parts by mass | — | — | — | — | — | — | — | — |
| | Curing agent | parts by mass | 0.5 | — | 0.5 | — | — | — | — | 0.5 |
| | Isophorone | parts by mass | 30.0 | 30.0 | 30.0 | 30.0 | 30.0 | 30.0 | 30.0 | 30.0 |
| | Scale-like silver powder | parts by mass | 52.0 | 52.0 | 52.0 | — | — | 52.0 | 52.0 | 56.0 |
| | Amorphous silver powder 1 | parts by mass | — | — | — | 52.0 | 52.0 | — | — | — |
| | Amorphous silver powder 2 | parts by mass | — | — | — | — | — | — | — | — |
| | Barium sulfate A | parts by mass | 6.0 | 6.0 | 6.0 | 6.0 | 6.0 | — | — | 2.0 |
| | Barium sulfate B | parts by mass | — | — | — | — | — | 6.0 | — | — |
| | Barium sulfate C | parts by mass | — | — | — | — | — | — | 6.0 | — |
| | Titanium oxide D | parts by mass | — | — | — | — | — | — | — | — |
| | Specific resistance | Ω cm | $5 \times 10^{-4}$ | $4 \times 10^{-4}$ | $5 \times 10^{-4}$ | $5 \times 10^{-4}$ | $7 \times 10^{-4}$ | $1 \times 10^{-3}$ | $2 \times 10^{-3}$ | $7 \times 10^{-4}$ |
| | Migration resistance | | good | good | good | good | good | good | good | good |
| | Repeated stretching durability | (times) | 2500 | 2550 | 1200 | 1450 | 3150 | 1000 | 850 | 1800 |
| | Surface feeling | | good | good | good | good | good | good | fair | good |
| | Wiring resistance | Ω/cm | 0.035 | 0.03 | 0.035 | 0.034 | 0.05 | 0.07 | 0.14 | 0.05 |
| | Load at 10% stretching | N | 89 | 46 | 33 | 32 | 64 | 54 | 56 | 83 |
| | Resistance ratio at 20% stretching | fold | 3.6 | 3.5 | 3.4 | 2.1 | 2.2 | 3.5 | 3.2 | 3.4 |

TABLE 4-2

| | Conductive paste | | Example 20 C9 | Example 21 C10 | Example 22 C11 | Example 23 C12 | Comparative Example 5 C13 | Comparative Example 6 C14 | Comparative Example 7 C15 | Comparative Example 8 C16 |
|---|---|---|---|---|---|---|---|---|---|---|
| Compounded composition | Epoxy resin*1) | parts by mass | 1:5 | 1.5 | — | — | 3.5 | 5.5 | 7.5 | 11.5 |
| | Stretchable resin (R1) | parts by mass | 10.0 | 10.0 | — | — | 8.0 | 6.0 | — | — |
| | Stretchable resin (R2) | parts by mass | — | — | 6.0 | — | — | — | — | — |
| | Stretchable resin (R3) | parts by mass | — | — | — | — | — | — | 4.0 | — |
| | Stretchable resin (R4) | parts by mass | — | — | — | — | — | — | — | — |
| | Stretchable resin (R5) | parts by mass | — | — | 6.0 | — | — | — | — | — |
| | Stretchable resin (R6) | parts by mass | — | — | — | 12.0 | — | — | — | — |
| | Curing agent | parts by mass | 0.5 | 0.5 | — | — | 0.5 | 0.5 | 0.5 | 0.5 |
| | Isophorone | parts by mass | 30.0 | 30.0 | 30.0 | 30.0 | 30.0 | 30.0 | 30.0 | 30.0 |
| | Scale-like silver powder | parts by mass | 58.0 | 43.0 | — | — | 52.0 | 58.0 | 58.0 | — |

TABLE 4-2-continued

| Conductive paste | | Example 20 C9 | Example 21 C10 | Example 22 C11 | Example 23 C12 | Comparative Example 5 C13 | Comparative Example 6 C14 | Comparative Example 7 C15 | Comparative Example 8 C16 |
|---|---|---|---|---|---|---|---|---|---|
| Amorphous silver powder 1 | parts by mass | — | — | — | 56.0 | — | — | — | 58.0 |
| Amorphous silver powder 2 | parts by mass | — | — | 58.0 | — | — | — | — | — |
| Barium sulfate A | parts by mass | — | 15.0 | — | 2.0 | — | — | — | — |
| Barium sulfate B | parts by mass | — | — | — | — | — | — | — | — |
| Barium sulfate C | parts by mass | — | — | — | — | 6.0 | — | — | — |
| Titanium oxide D | parts by mass | — | — | — | — | — | — | — | — |
| Specific resistance | Ω cm | $6 \times 10^{-4}$ | $1 \times 10^{-3}$ | $3 \times 10^{-4}$ | $6 \times 10^{-4}$ | $5 \times 10^{-3}$ | $7 \times 10^{-4}$ | $2 \times 10^{-4}$ | $1 \times 10^{-4}$ |
| Migration resistance | | good | good | good | poor | good | good | good | good |
| Repeated stretching durability | (times) | 450 | 500 | 400 | 2350 | 5 | 2 | 0 | 0 |
| Surface feeling | | good | fair | good | good | poor | fair | fair | fair |
| Wiring resistance | Ω/cm | 0.04 | 0.07 | 0.02 | 0.04 | 0.35 | 0.05 | 0.014 | 0.007 |
| Load at at 10% stretching | N | 86 | 91 | 45 | 56 | 140 | 3800 | breaking of wiring | breaking of wiring |
| Resistance ratio at 20% stretching | fold | 2.8 | 2.9 | 2.1 | 1.9 | 56.8 | 25000 | breaking of wiring | breaking of wiring |

Application Example 1

The conductive paste obtained in Example 12 was applied onto a release sheet with a bar coater and dried in a hot-air drying oven of 120° C. for 30 minutes or longer, and the similar operation was repeated as necessary such that the thickness of the stretchable conductor layer became 70 μm to produce a sheet-like stretchable conductor layer with a release sheet.

The stretchable conductor composition sheet cut into a length of 190 mm and a width of 10 mm obtained in Example 12 was stacked on the central portion of a hot-melt urethane sheet (first insulating layer) having a length of 200 mm, a width of 30 mm and a thickness of 50 μm, and a polyurethane sheet (second insulating layer: cover coat layer) having a length of 150 mm and a width of 25 mm was further stacked thereon such that 20 mm of both ends of the stretchable conductor composition sheet was each exposed. Next, a 2-way tricot fabric ("KNZ2740" manufactured by GUNSEN, nylon yarn:urethane yarn=63%:37% (blend ratio), areal weight: 194 g/m²) having a length of 210 mm and a width of 50 mm was stacked so as to be in contact with the above-mentioned first insulating layer, and all of these were bonded using a hot press to obtain a stretchable conductor composition sheet laminated on the fabric. Repeated stretching durability (number of times) for the obtained sheet sample was determined in the same manner as in Example 12. As a result, the sheet sample exhibited excellent properties of repeated stretching durability of 2500 times.

Application Example 2

In the same manner as in Application Example 1, a circular electrode having a diameter 50 mm was formed from the stretchable conductor composition sheet on the intersection of each of left and right posterior axillary lines and the seventh rib, and a stretchable conductor composition sheet wiring having a width of 10 mm was formed from each of the circular electrodes to the center of the chest on the inside of a sports shirt. The contour line of the joint between the electrode portion and the wiring portion contour line was smoothly processed with an R10mm. Note that the wirings extending from the left and right electrodes to the center of the chest have a gap of 5 mm therebetween at the center of the chest, and both wirings were not short-circuited. The first insulating layer was made 5 mm larger than the outline of the stretchable conductor composition sheet. The cover coat layer of the wiring portion had a width of 16 mm and a size enough to cover up to 3 mm outside from the stretchable conductor composition sheet, and the edge 10 mm on the chest center side of the wiring formed from the stretchable conductor composition sheet was not covered with the cover coat layer. The cover coat layer of the electrode portion was covered concentrically with the electrode and in a ring shape having an inner diameter of 44 mm and an outer diameter of 56 mm, and the joint between the electrode portion and the wiring portion was also covered up to 3 mm outside.

Subsequently, a stainless steel hook was attached on a surface side of the sport shirt at the edge of the center of the chest where no cover coat layer of the left and right wiring portions was disposed, and in order to ensure electrical continuity with the wiring portion on a back side of the surface, the stainless steel hook was electrically connected to the stretchable conductor composition layer using a conductive yarn in which a fine metal wire was twisted.

Heart rate sensor WHS-2 manufactured by Union Tool Co. was connected via the stainless steel hook, and was programed so that a heart rate data could be received with a smartphone manufactured by Apple on which the application "myBeat" designed specifically for the heart rate sensor WHS-2 had been installed to be displayed on its screen. In this way, the sports shirt in which a heart rate measurement function was incorporated was produced.

This shirt was worn by a subject, and electrocardiogram data of the subject was acquired during being at rest, walking, running, riding a bicycle, driving a car, and sleeping. The acquired electrocardiogram data had less noise and a high resolution, and hence had a quality as an electrocardiogram that is capable of analyzing mental states, physical condition, fatigue, sleepiness, stress levels, or the like can be analyzed from the change in heart rate interval, the electrocardiogram waveform, and the like.

Likewise, using the stretchable conductor composition sheets of Example 5, Example 6, Example 7, Example 11, and Comparative Example 1, sports shirts in which a heart rate measurement function was incorporated were obtained in the same manner as above. As a result, each of the Examples could acquire excellent electrocardiogram data except that as for the stretchable conductor composition of Example 7, noise was occasionally observed when running, and as for the stretchable conductor composition of Comparative Example 1, it was impossible to measure the heart rate because of disturbed waveforms during rigorous running. The obtained results corresponded to the quality of the surface feeling of the stretchable conductor composition. It was assumed that the surface feeling relates to roughness of the surface, and it was suggested that particularly when the subject severely moves, the contact between the subject's body surface and the electrode surface may become poor.

Application Example 3

The conductive paste obtained in Example 13 was applied onto a release sheet and dried in a hot-air drying oven of 120° C. for 30 minutes or longer to produce a sheet-like stretchable conductor layer with a release sheet having a thickness of 45 μm.

Next, a polyurethane hot-melt sheet was laminated on the conductive sheet with a release sheet using a hot press, and then punched out in a length of 190 mm and a width of 10 mm to obtain a three-layer sheet having a configuration of release sheet/stretchable conductor composition/polyurethane hot-melt sheet.

Next, the obtained three-layer sheet was stacked on the center portion of a 2-way tricot fabric ("KNZ2740" manufactured by GUNSEN, nylon yarn:urethane yarn=63%:37% (blend ratio), areal weight: 194 g/m$^2$) having a length of 200 mm and a width of 30 mm such that the hot-melt sheet side of the three-layer sheet was in contact with the fabric, and they were bonded using a hot press to obtain a stretchable electrode sheet. A hot-melt urethane sheet having a length of 150 mm and a width of 25 mm was further stacked on the stretchable conductor composition layer of the stretchable electrode sheet such that 20 mm of both ends of the stretchable conductor composition layer was each exposed, and they were bonded using a hot press. Furthermore, the exposed portion of the stretchable conductor composition layer was coated with a stretchable carbon paste by screen printing so as to be covered with a rectangle having a length of 22 mm and a width of 14 mm to obtain a stretchable composite electrode sheet.

The obtained stretchable composite sheet was punched out in a length of 194 mm and a width of 14 mm so as not to cut across the stretchable conductor composition layer, and the punched out sheet was bonded on a region from a side portion to a center portion on the rear side of the cup under part of sports brassiere using a hot-melt sheet in such a manner that the carbon paste coating layer faced a skin side. The carbon paste coating layer on the side portion serves as an electrode portion in contact with a body. A stainless steel hook was attached on the outer side corresponding to each of the left and right carbon paste coating portions opposing to the center portion of the brassiere, and electrically connected to the stretchable conductor composition layer using a conductive yarn in which a fine metal wire was twisted. Heart rate sensor WHS-2 manufactured by Union Tool Co. was connected via the stainless steel hook, and was programed so that a heart rate data could be received with a smartphone manufactured by Apple on which the application "myBeat" designed specifically for the heart rate sensor WHS-2 had been installed and to be displayed on its screen. In this way, the sports brassiere in which a heart rate measurement function was incorporated was produced.

This sports brassiere was worn by a subject, and electrocardiogram data of the subject was acquired during being at rest, walking, running, riding a bicycle, driving a car, and sleeping. The acquired electrocardiogram data had less noise and a high resolution, and hence had a quality as an electrocardiogram that is capable of analyzing mental states, physical condition, fatigue, sleepiness, stress levels, or the like from the change in heart rate interval, the electrocardiogram waveform, and the like.

Likewise, sports brassieres in which a heart rate measurement function was incorporated were produced in the same manner as above except that the pastes of Examples 13 to 23 were used. As a result, each of the Examples could acquire excellent electrocardiogram data.

Application Example 4

A cover coat layer composed of urethane resin having stretchability was formed on a release sheet, a stretchable carbon paste was then formed on a portion corresponding to an electrode by screen printing, and dried and cured. Next, a paste composed of the stretchable conductor composition obtained in Example 22 was overlaid and printed thereon, and dried and cured. Further thereon, a urethane resin layer having hot-melt property was similarly overlaid and printed by screen printing. The pattern of the stretchable conductor composition layer is shown in the Drawing. The portion on which the carbon paste was overlaid is a portion having a wiring length of 15 mm at the end of a wrist side.

The urethane sheet having hot-melt property side of the resulting overlaid printed product was laminated on the back side of a fabric glove, and the wiring was transferred from the release sheet to the glove using a hot press to obtain a glove with a wiring. Lead wires were attached to the electrodes in a portion corresponding to a wrist of the obtained glove with a wiring by using a conductive adhesive to achieve such a configuration that the resistance change of the wiring in accordance with bending of each finger joint can be read by a multichannel resistance meter.

Using the obtained device configuration, first, a user wore a glove type input device on the right hand, a resistance value of a portion corresponding to each finger joint in a state where the user opens the hand, which is a state of "paper" of scissors-paper-rock, was set as an initial value, and a resistance value in a state where the user holds the hand, which is a state of "rock" of scissors-paper-rock, was set as a limit value. A range of change in resistance of each finger joint between these two states was divided into 64 gradations, by bring the 64 gradations into correspondence with bending states of finger joints, a three-dimensional image of CG-synthesized fingers by software was operated.

The movement of the resulting CG fingers was natural, smooth and excellent. In addition, it was also possible to replicate complex movement such as "scissors-paper-rock" and fingerspelling.

INDUSTRIAL APPLICABILITY

The present invention provides a stretchable electrode and a stretchable wiring capable of maintaining high electrical conductivity even if being stretched, and a biological information measurement interface in which the stretchable electrode and a stretchable wiring are laminated on a substrate such as a garment, a belt, a brassiere, or the like, and is suitably utilized in the medical field and the health monitoring field.

The invention claimed is:
1. A stretchable conductive sheet comprising:
a first insulating layer and a stretchable conductor layer provided on the first insulating layer, wherein the stretchable conductor layer contains a resin having an elastic modulus of 30 MPa to 1000 MPa, and has an electric resistance of 300 Ω/cm or less,
wherein a load, when the stretchable conductive sheet is stretched at a stretching rate of 10% of the stretchable conductive sheet, is 100 N or less.

2. The stretchable conductive sheet according to claim 1, wherein the stretchable conductor layer has an initial sheet resistance of 1Ω square or less.

3. The stretchable conductive sheet according to claim 1, wherein, when the stretchable conductive sheet is stretched at a stretching rate of 20% of stretchable conductive sheet, the stretchable conductive sheet has a change in electric resistance of less than 5-fold.

4. The stretchable conductive sheet according to claim 1, wherein the stretchable conductor layer further comprises a conductive filler.

5. The stretchable conductive sheet according to claim 1, wherein the stretchable conductive sheet has a thickness of 200 μm or less.

6. The stretchable conductive sheet according to claim 1, wherein the stretchable conductor layer further comprises conductive particles, and
wherein the resin is contained in an amount of 7 to 35% by mass relative to a total amount of the conductive particles and the resin.

7. The stretchable conductive sheet according to claim 6, wherein the conductive particles comprise silver particles having an average particle diameter, as measured by a dynamic light scattering method, of 0.5 to 20 μm.

8. The stretchable conductive sheet according to claim 1, wherein the stretchable conductor layer further comprises conductive particles and barium sulfate particles, and
wherein the barium sulfate particles are contained in an amount of 2 to 30% by mass relative to a total amount of the conductive particles and barium sulfate particles, and the resin is contained in an amount of 7 to 35% by mass relative to the total amount of the conductive particles, barium sulfate particles and the resin.

9. The stretchable conductive sheet according to claim 8, wherein an average particle diameter of the conductive particles as measured by a dynamic light scattering method is larger than an average particle diameter of the barium sulfate particles as measured by a dynamic light scattering method.

10. The stretchable conductive sheet according to claim 8, wherein the barium sulfate particles are surface treated barium sulfate particles obtained by subjecting the barium sulfate particles to a surface treatment with a hydroxide and/or oxide of one or both of Al and Si.

11. A biological information measurement interface comprising a substrate on which the stretchable conductive sheet according to claim 1 is laminated,
wherein the substrate is a strip-shaped material configured to be attached at least in a circumferential direction of a trunk of a human body, and/or a garment having a woven or knitted fabric or a non-woven fabric.

12. The biological information measurement interface according to claim 11, wherein the strip-shaped material is a belt or a brassiere.

13. The stretchable conductive sheet according to claim 1, further comprising a second insulating layer provided on the stretchable conductor layer.

* * * * *